(12) United States Patent
Yamamura et al.

(10) Patent No.: US 10,539,540 B2
(45) Date of Patent: Jan. 21, 2020

(54) LIQUID CHROMATOGRAPH AND METHOD FOR CORRECTING DETECTOR OUTPUT VALUE FLUCTUATION OF LIQUID CHROMATOGRAPH

(71) Applicant: HITACHI HIGH-TECH SCIENCE CORPORATION, Minato-ku, Tokyo (JP)

(72) Inventors: Shuhei Yamamura, Tokyo (JP); Daisuke Akieda, Tokyo (JP); Ayumi Nakaogami, Tokyo (JP); Katsutoshi Shimizu, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 344 days.

(21) Appl. No.: 15/617,790

(22) Filed: Jun. 8, 2017

(65) Prior Publication Data

US 2017/0356887 A1    Dec. 14, 2017

(30) Foreign Application Priority Data

Jun. 10, 2016  (JP) ................................ 2016-127042
Jun. 7, 2017   (JP) ................................ 2017-112495

(51) Int. Cl.
| | | |
|---|---|---|
| *G01N 30/60* | (2006.01) | |
| *G01N 21/64* | (2006.01) | |
| *G01N 30/16* | (2006.01) | |
| *G01N 30/74* | (2006.01) | |
| *G01N 30/02* | (2006.01) | |

(52) U.S. Cl.
CPC ......... *G01N 30/60* (2013.01); *G01N 21/6428* (2013.01); *G01N 30/16* (2013.01); *G01N 30/74* (2013.01); *G01N 2030/027* (2013.01)

(58) Field of Classification Search
None
See application file for complete search history.

(56) References Cited

U.S. PATENT DOCUMENTS

| | | | | |
|---|---|---|---|---|
| 2005/0009114 A1* | 1/2005 | Korbling | .......... | G01N 33/56977 435/7.2 |
| 2007/0004044 A1* | 1/2007 | Ramsay | ............. | G01N 33/5005 436/86 |

(Continued)

FOREIGN PATENT DOCUMENTS

| | | |
|---|---|---|
| JP | 2011-058930 A | 3/2011 |
| JP | 5448224 B1 | 3/2014 |

OTHER PUBLICATIONS

Xiaoran Ning, Chromatogram baseline estimation and denoising using sparsity, Sep. 21, 2014, 23 pages (Year: 2014).*

(Continued)

*Primary Examiner* — Tung S Lau
(74) *Attorney, Agent, or Firm* — Brinks Gilson & Lione

(57) ABSTRACT

A minimum peak is determined from analysis results, a correction wavelength at which an S/N ratio of the minimum peak is greatest is determined, and the determined correction wavelength is used to execute correction of the minimum peak. A plurality of detector output value correction method are registered in a processor, correction method is selected from default correction method or from among a plurality of preset correction methods according to an object to perform correction.

7 Claims, 12 Drawing Sheets

(56) References Cited

U.S. PATENT DOCUMENTS

2012/0096919 A1* 4/2012 Choikhet ............... G01N 30/24
73/1.02
2014/0268154 A1 9/2014 Yamaguchi et al.
2017/0010269 A1* 1/2017 Pennington ...... G01N 33/57434

OTHER PUBLICATIONS

Mark Stephen Jeansonne, Chromatographic Peak Shape Analysis and Modeling, 268 pages, 1990 (Year: 1990).*
Francesc Fern_andez Albert, Machine Learning Methods for the Analysis of Liquid Chromatography-Mass Spectrometry datasets in Metabolomics, 216 pages, Oct. 2014 (Year: 2014).*
Tom Kupiec, Quality-Control Analytical Methods: High-Performance Liquid Chromatography, Jun. 2004, 5 pages (Year: 2004).*
Jennifer Listgarten, Statistical and Computational Methods for Comparative Proteomic Profiling Using Liquid Chromatography-Tandem Mass Spectrometry, 16 pages, 2005 (Year: 2005).*
Chromatographic and Electrophoretic Methods chaptet 12, printed on Sep. 19, 2019 (Year: 2019).*

* cited by examiner

LIQUID CHROMATOGRAPH AND METHOD FOR CORRECTING DETECTOR OUTPUT VALUE FLUCTUATION OF LIQUID CHROMATOGRAPH

RELATED APPLICATIONS

This application claims priority under 35 U.S.C. § 119 to Japanese Patent Applications No. 2016-127042 filed on Jun. 10, 2016 and No. 2017-112495 filed on Jun. 7, 2017, the entire contents of which are hereby incorporated by reference.

BACKGROUND OF THE INVENTION

1. Field of the Invention

The present disclosure relates to a liquid chromatograph having function of correcting detector output fluctuation and a method for correcting detector output value fluctuation of liquid chromatograph.

2. Description of the Related Art

In performing an analysis using a liquid chromatography, the output value of a detector fluctuates due to various disturbances, which adversely influences results of the analysis. In this disclosure, detector output value fluctuation will refer to fluctuations in the signal strength of the detector caused by disturbances.

In a gradient elution method in which a mobile phase is analyzed while being mixed, there is a case in which slight changes in the concentration of the mobile phase which is not completely mixed are detected as detector output value fluctuation. There is a case in which pressure (flow rate) fluctuation of a liquid pump device becomes a change in refractive index and is detected as detector output value fluctuation. Since the detector output value fluctuation adversely influences the analysis results, in the gradient elution method, it is preferable that the mobile phase is mixed completely uniformly. However, in a case in which a mobile phase which is difficult to mix, a large volume mixer must be used, and adverse effects such as degradation of gradient responsiveness and a delay in the analysis time. Positional changes of the configuration components and detector output value fluctuation caused by changes in the usage environmental temperature and humidity of the analysis device influence the analysis results. As one solution to this problem, there is a method in which the influence of disturbances is removed by measuring detector output value fluctuation caused by disturbances at the same time as analysis and performing a correction process which subtracts the detector output value fluctuation from the analysis results, and stabilized analysis is performed.

A method of correcting by averaging different wavelengths from a measurement wavelength which is acquired at the same time as the detection wavelength is depicted as a process of correcting a drift waveform of a multichannel detector (see, for example, Japanese Patent No. 5448224).

A method is depicted in which noise which is a cause of the detector output value fluctuation is calculated and a ratio of a detected component signal strength to a noise signal strength (hereinafter the S/N ratio) is automatically calculated (see, for example, JP-A-2009-208273).

In a known method of correcting detector output value fluctuation, a user sets a correction wavelength from a large amount of data and recalculates the analysis results.

Specifically, in a case in which analysis results such as those illustrated in FIGS. 1 and 2 are obtained, a wavelength $\lambda 2$, $\lambda 3$, $\lambda n$ or the like which does not have strong absorption in a range of measuring, unlike a measurement wavelength $\lambda 1$, is selected and the detector output value fluctuation is corrected using subtraction. In this case, the selection of the correction wavelength is influenced by the experience of the user. When an excessive correction process is carried out, information of minute components which are detected as minute chromatographic peaks is lost, and it may not be possible to obtain accurate examination results. It is difficult to select an optimum detector output value fluctuation correction method for obtaining accurate examination results, and even skilled users have different determination criteria of the selected correction wavelength and the like, and thus, each time measurement or examination is performed, there is a possibility that the results may be different. In a case in which the amount of data is great, the burden on the user increases, and it takes the time to obtain the object examination results.

SUMMARY OF THE INVENTION

The present disclosure has been made in view of the above-described circumstances, and one of objects of the present disclosure is to provide a liquid chromatograph and a method for easily reducing detector output value fluctuation to obtain qualitative and quantitative results with high sensitivity and good reproducibility with respect to minute chromatographic peaks which originate from minute components.

The term chromatographic peak indicates a change amount in the signal strength of a detector originating from the sample. In the present disclosure, the chromatographic peak is simply referred to as "peak."

According to an exemplary embodiment of the present disclosure, there is provided a method for correcting detector output value of a liquid chromatograph, the method including: selecting an analysis condition for using a liquid chromatograph, the analysis condition being selected from preset recipes that are registered in advance according to an examination object, the analysis condition being a condition to be set with respect to devices included in the liquid chromatograph such as a pump, an auto sampler, a column oven, and a detector, starting analysis according to the analysis condition that is selected in the previous step, measuring a characteristic of a sample using the detector, the characteristic including at least one of an absorbency and a fluorescence amount, and storing and displaying a signal strength of the detector indicating the characteristic of the sample in relation to time as analysis results; obtaining a chromatogram; recognizing peaks included in the chromatogram; determining a most minute peak of the signal strength of the analysis results in peaks which are recognized as a correction target peak; determining correction candidate wavelengths with respect to the correction target peak; performing a correction process on detector output value fluctuation based on correction method which is selected from among a plurality of preset correction methods; and outputting the analysis conditions, the correction condition, and corrected results of the characteristic of the sample.

According to another exemplary embodiment of the present disclosure, there is provided a liquid chromatograph including: a pump that pumps a mobile phase; an auto sampler that injects a sample; a column oven that maintains a column that separates components at a constant temperature; a detector that detects separated components; a processor that selects a recipe during measurement from analysis conditions which are preset in advance, selects detector output value correction process method which is registered, and examines analysis results; a data storage that stores the analysis results and examination results; and a display unit that displays the analysis conditions, the analysis results, and the examination results, wherein the processor operates to perform a process including: selecting analysis conditions from a recipe which is registered in advance according to an examination object; performing analysis according to the selected analysis conditions; measuring a characteristic of a sample, the characteristic including at least one of an absorbency and a fluorescence amount; determining a signal strength of the detector such as the absorbency or the fluorescence amount of the sample as analysis results; recognizing peaks included in the chromatogram; setting a minimum peak from among the recognized peaks as a correction target peak; selecting a correction candidate wavelength for the correction target peak; selecting detector output value correction method which is registered in advance; and performing a correction process based on the selected detector output value correction method.

According to another exemplary embodiment of the present disclosure, there is provided a liquid chromatograph including: a pump that pumps a mobile phase; an auto sampler that injects a sample; a column oven that maintains a column that separates components at a constant temperature; a detector that detects separated components; a processor that selects a recipe during measurement from analysis conditions which are preset in advance, selects detector output value correction process method which is registered, and examines analysis results; a data storage that stores the analysis results and examination results; and a display unit that displays the analysis conditions, the analysis results, and the examination results, wherein the processor operates to perform a process including: selecting analysis conditions from a recipe which is registered in advance according to an examination object; performing analysis according to the selected analysis conditions; measuring a characteristic of a sample, the characteristic including at least one of an absorbency and a fluorescence amount; determining a signal strength of the detector such as the absorbency or the fluorescence amount of the sample as analysis results; recognizing peaks included in the chromatogram; setting a plurality of peaks from among the recognized peaks as a correction target peaks; selecting a plurality of correction candidate wavelengths for the correction target peaks; selecting detector output value correction method which is registered in advance; and performing a correction process based on the selected detector output value correction method.

DETAILED DESCRIPTION OF THE PREFERRED EMBODIMENTS

Embodiments according to the present disclosure will be described below with reference to the drawings.

Figure 10:
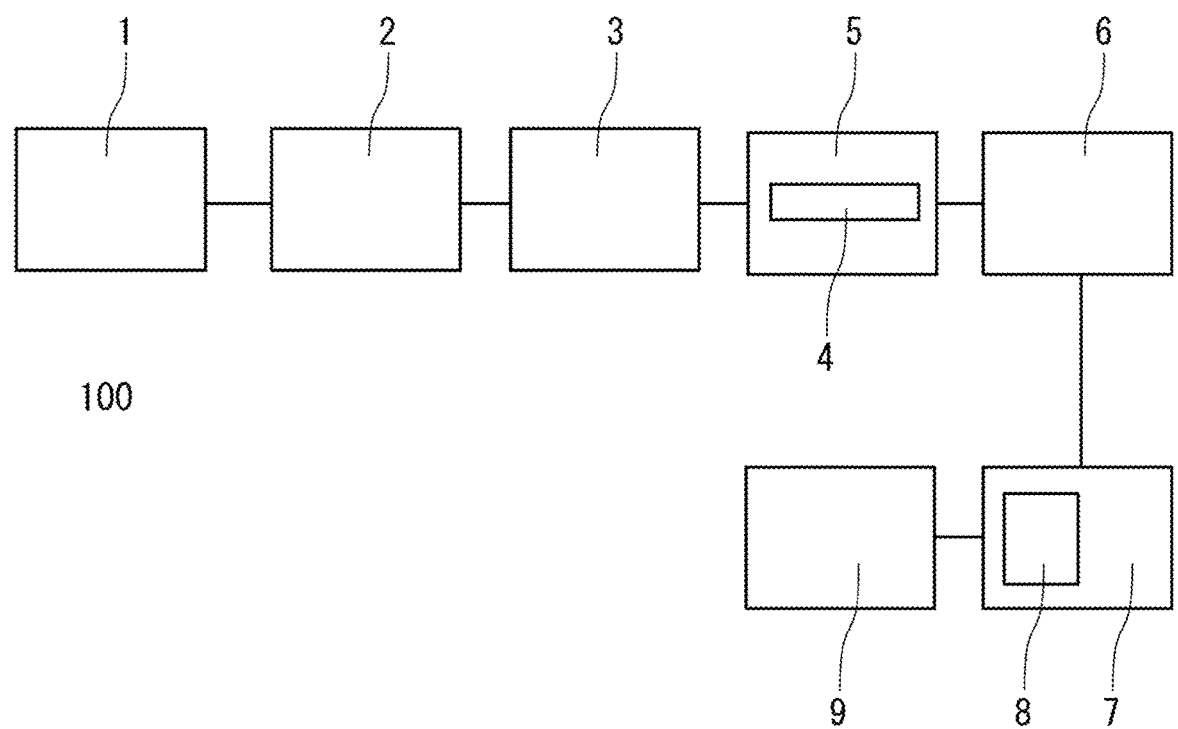
FIG. 10 is a device configuration diagram of a liquid chromatograph.

As illustrated in FIG. 10, a liquid chromatograph according to the present disclosure includes a pump 2, an auto sampler 3, a column oven 5, a detector 6, a processor 7, a data storage 8, and a display unit 9. The pump 2 pumps the mobile phase, the auto sampler 3 injects the sample, the column oven 5 maintains a column 4 which separates components at a constant temperature, the detector 6 detects the separated components, the processor 7 registers, selects and executes the analysis conditions and the method for correcting detector output value fluctuation and examines the analysis results, the data storage 8 stores the analysis results and the examination results, and the display unit 9 displays the analysis results, the examination results, and the method for correcting detector output value fluctuation. The detector 6 has a plurality of elements which detect signal strength, and a three-dimensional detector which is capable of acquiring the signal strength with respect to the time for a plurality of wavelengths.

Next, description will be given of the detector output value fluctuation correction of a liquid chromatograph according to the present disclosure using FIG. 3. First, in the correction target peak determination flow, a peak which originates from the sample is identified from the analysis data, is compared to a threshold which is set in advance, and peak presence or absence determination is performed. In a case in which there are no peaks greater than or equal to the threshold, that is, when it is determined that the measurement target component is absent, the examination is ended. In a case in which it is determined that a peak is present, the minimum peak which is identified is determined as the correction target peak. Here, by setting the minimum peak which originates from the sample as the correction target peak, the correction criteria is defined, the minimum peak, that is, the minute component is also detected without being buried in the correction process, and it is possible to obtain qualitative and quantitative examination results.

Next, in the correction wavelength determination flow, the presence or absence of peaks is identified in wavelengths which are different from the measurement wavelength which originates from the sample, and the wavelengths in which peaks are absent are extracted as the correction candidate wavelengths. Here, from the extracted correction candidate wavelengths, the correction wavelength which is suitable for a detector output value fluctuation correction process such as maximization of the S/N ratio or optimization of the reproducibility of the S/N ratio in comparison to the S/N ratio of the previously determined correction target peak is selected, and the correction process is executed.

In the present disclosure, a ratio between a detector output signal of the correction target peak and a detector output signal in the correction wavelength is simply referred to as "S/N ratio."

According to the procedure described above, since it is possible to obtain the examination results without losing the minute peaks which originate from the minute components of the sample due to the correction process by performing the detector output value fluctuation correction, and to determine the correction wavelength which is used for the correction target peak and the detector output value fluctuation correction process based on fixed determination criteria, it becomes possible to obtain qualitative and quantitative examination results under the same criteria without the correction method by the user, the reexamination time, or the like being different. Since the analysis and the examination caused to proceed based on the correction target peak determination flow and the correction wavelength determination flow, the operation method is simple for the user.

The present disclosure may be applied to a two-dimensional detector which has a function of acquiring the signal strengths of a plurality of wavelengths at substantially the same time by switching the wavelength at high speed.

Hereinafter, the detector output value fluctuation correction process will be indicated according to the procedure.

Hereinafter, description will be given of the means for the detector output value fluctuation correction of the present disclosure in order.

Figure 1:
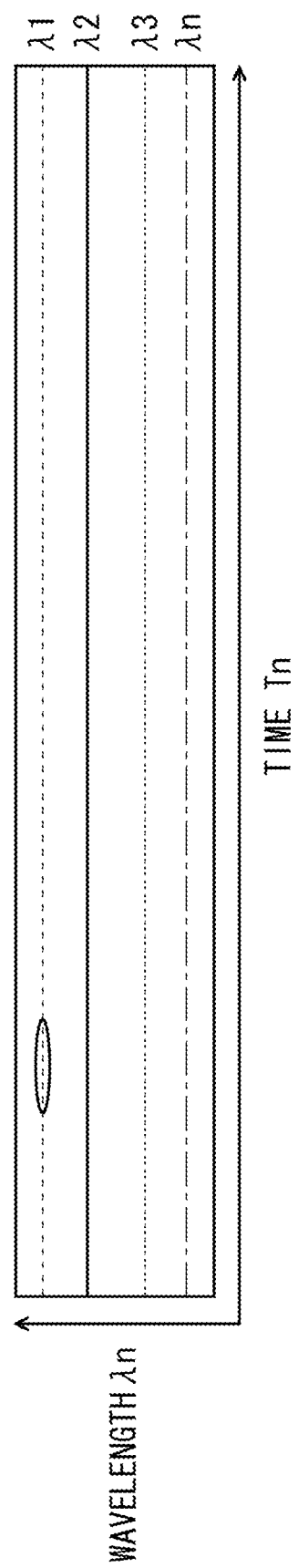
FIG. 1 is a detector output value display example in time Tn of a measurement wavelength $\lambda 1$ and all measurement wavelengths $\lambda 2$ to $\lambda n$.
Figure 2:
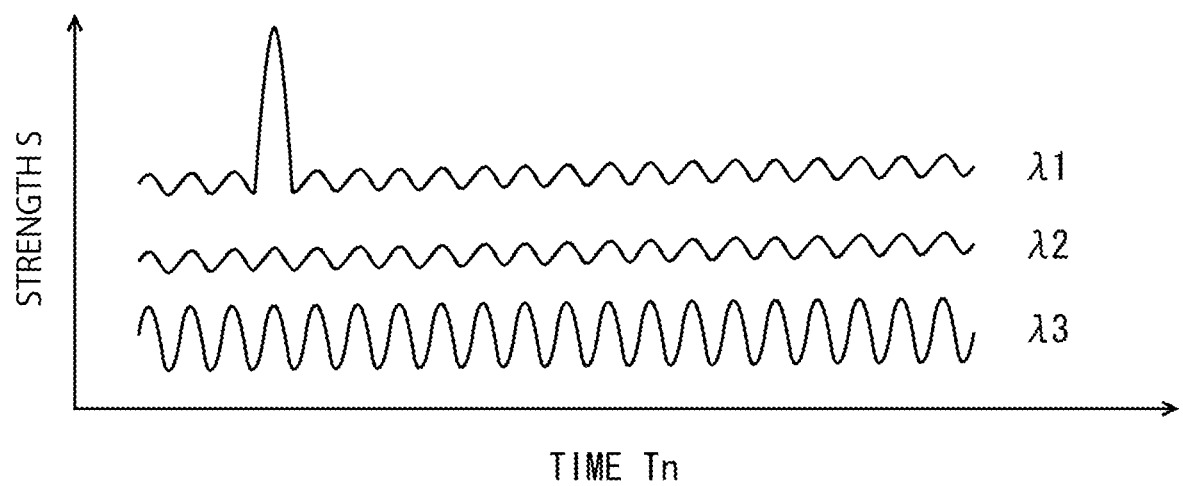
FIG. 2 is a detector output value display example in the time Tn of the measurement wavelength $\lambda 1$ and correction candidate wavelengths $\lambda 2$ and $\lambda 3$.
Figure 3:
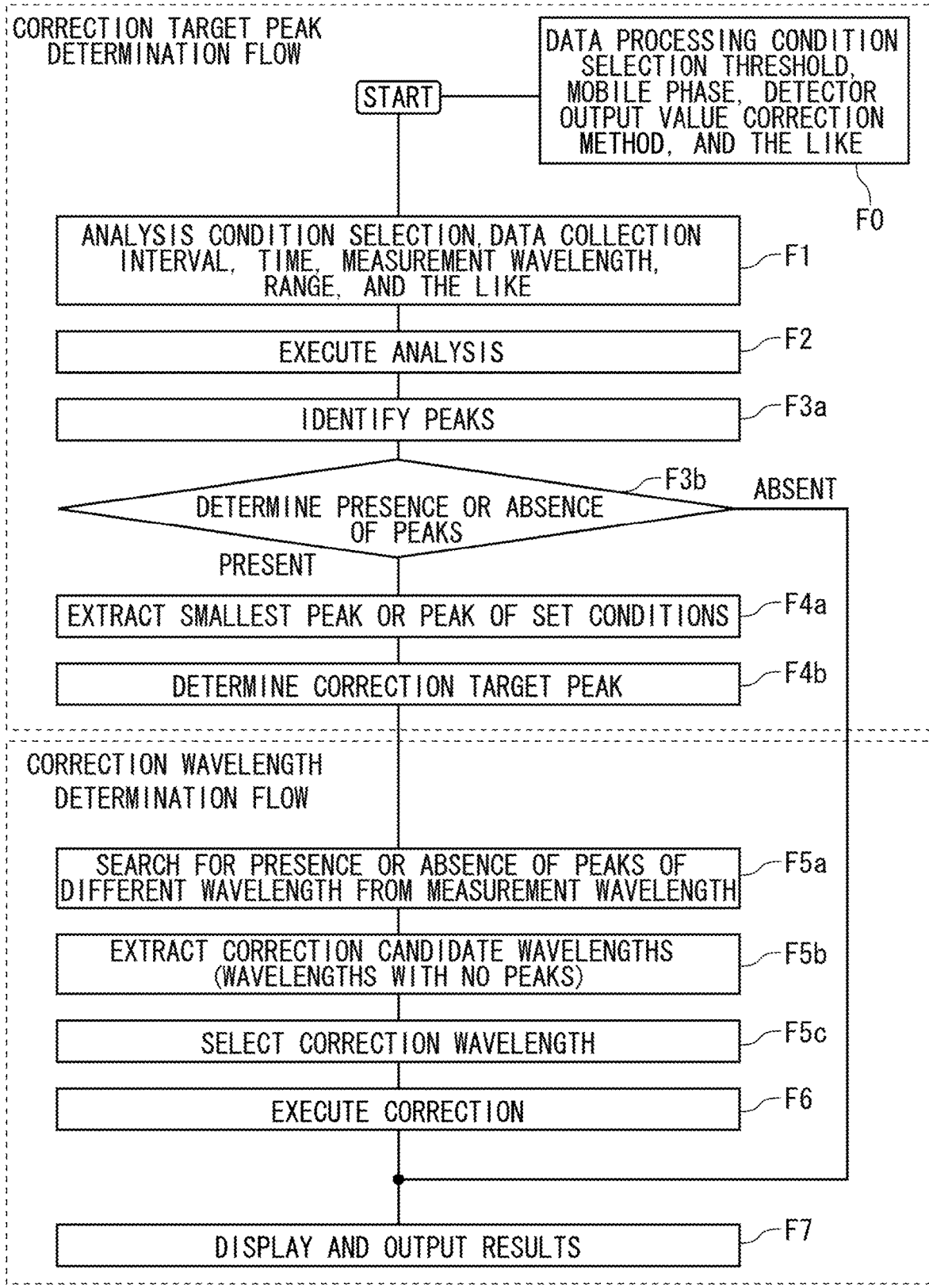
FIG. 3 is an analysis flow in which detector output value fluctuation correction is performed.

FIG. 3 illustrates an analysis flow in which the detector output value fluctuation correction is performed. The correction target peak determination flow of which is depicted in the top portion of FIG. 3 is common to all of the means, and the correction wavelength determination flow which is depicted in the bottom portion of FIG. 3 is different for each of the means which are indicated below, and thus, description will be given for each of the means.

(Correction Target Peak Determination Flow)

First, in the correction target peak determination flow, the user selects the analysis conditions such as the data collection time, the data collection interval, the measurement wavelength, and the measurement wavelength range of the detector from recipes that are registered in advance (F1). Next, the sample is injected, and, based on the selected analysis conditions, the analysis is executed (F2). Next, the analysis results are examined and the determination of the peak presence or absence (F3$b$) is performed. As an example of a method for determining the presence or absence of peaks, there is a method in which the measurement wavelength is compared to a threshold which is set in advance, and in a case in which the signal strength is greater than or equal to the threshold, the measurement wavelength is determined to be a peak, and in a case in which the signal strength is less than or equal to the threshold, the measurement wavelength is determined not to be a peak. In the determination method, a noise level nominal value of the detector is registered using the threshold for determining peaks as an initial value; however, it is possible for the user to separately register the noise level nominal value according to the object and the concentration and usage amount of the analysis sample. It is also possible to register the baseline noise which is obtained from the examination value of the measurement results as an initial value. In a case in which it is detected that the peak is present, the signal strengths of a plurality of peaks of the obtained analysis results are compared, the minimum peak which originates from the sample components is determined and is determined as the correction target peak (F4$b$). It is also possible to select a plurality of peaks to be correction targets, and the user may arbitrarily set one or more peaks.

(Correction Wavelength Determination Flow)

Figure 11:
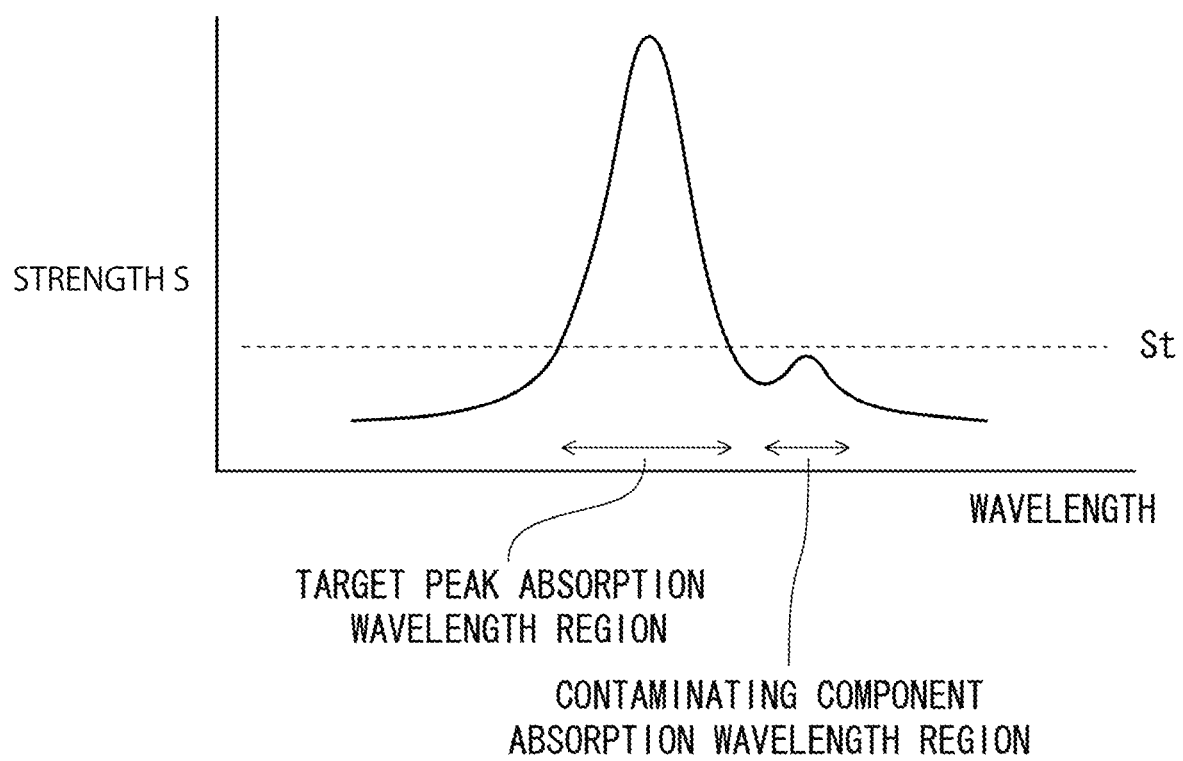
FIG. 11 is a diagram of a spectrum including a contaminating component.

(Method 1) The presence or absence of peaks in a measurement wavelength range and in a different wavelength region from the measurement wavelength is searched (F5$a$), and wavelengths with no peaks are extracted as correction candidate wavelengths (F5$b$). There is a method of extracting the correction candidate wavelengths from a smaller signal range than the threshold which is set in advance in the measured chromatogram, and a method of examining the spectrum of the correction target peak as means for extracting the correction candidate wavelengths. In a case in which the spectral data of the correction target peak is examined, a wavelength region in which the absorption of the correction target peak is great and a wavelength region in which the absorption is small are determined, and the correction candidate wavelengths are extracted from the wavelength region in which the absorption is small. For example, a method of setting, in advance, a threshold $S_t$ so as to extract the correction candidate wavelengths from less than or equal to a fixed absorption strength value, or a method of automatically determining a wavelength region which is small relative to the correction target peak strength can be considered as a method for determining the wavelength region in which the absorption is small. In order to realize a more accurate determination, the first derivative and the second derivative of the spectral data may be calculated. FIG. 11 illustrates a spectrum example in a case in which a contaminating component is included in the vicinity of the correction target peak. By ascertaining the spectral shape from df and ddf which are calculated from the derivatives, it is possible to extract the correction candidate wavelengths while avoiding the absorption wavelength region of the correction target peak and the contaminating component. Next, one wavelength is selected as the correction wavelength from the correction candidate wavelengths which are extracted such that the S/N ratio of the determined correction target peak is greatest (F5$c$), and detector output value fluctuation correction is executed based on the analysis flow (F6).

Figure 12:
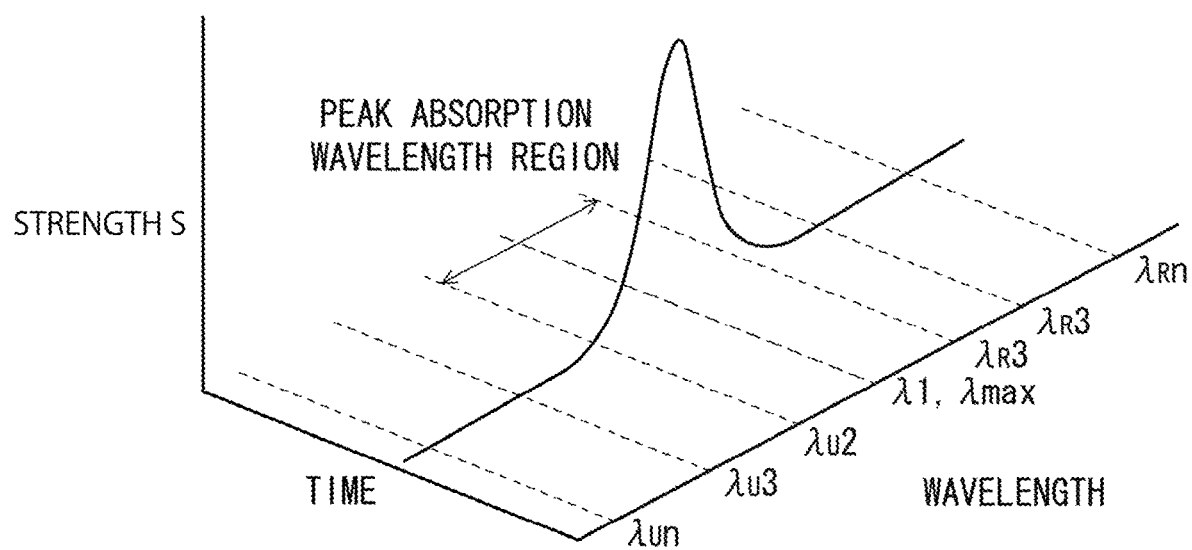
FIG. 12 is a conceptual diagram of an absorption spectrum when selecting correction candidate wavelengths.

It is preferable that the correction wavelength avoids the absorption wavelength region of the correction target peak and is close to a measurement wavelength $\lambda 1$ or a maximum absorption wavelength $\lambda$max. The correction candidate wavelengths are extracted from the short wavelength side and the long wavelength side centered on the measurement wavelength or the maximum absorption wavelength. FIG. 12 is a conceptual diagram of an absorption spectrum when select correction candidate wavelengths. First, a wavelength region in which the absorption signal is small is determined while avoiding the absorption wavelength region of the correction target peak, and wavelengths closest to the measurement wavelength or the maximum absorption wavelength are extracted as $\lambda_L 2$ and $\lambda_R 2$ from the short wavelength side and the long wavelength side, respectively. Next, the S/N ratio which is calculated using the extracted $\lambda_L 2$ and $\lambda_R 2$ are the correction candidate wavelengths is used as an initial value, and the wavelength at which the S/N ratio is greatest is searched while shifting the correction candidate wavelength. In each region of the short wavelength side and the long wavelength side, the magnitudes of the S/N ratio of λn and λn+1 are compared, and when the S/N ratio of λn+1 is smaller than the S/N ratio of λn, λn is set as a correction candidate wavelength λrwl. The S/N ratios for the correction candidate wavelengths λrwl which are extracted from each of the short wavelength side and the long wavelength side are compared, and the wavelength of the one with the greatest S/N ratio is used as the final correction wavelength.

By performing the detector output value fluctuation correction at which the S/N ratio of the minimum peak is greatest using the detector output value fluctuation correction as described in the above in the (Method 1) section, in a correction process of the related art, it becomes possible to perform qualitative and quantitative examination of the sample which includes a minute component which may be buried as noise. It is also anticipated that the S/N ratio may be improved using a plurality of peaks as targets as an adaptation of the correction method of (Method 1). In the analysis which uses the liquid chromatograph, a plurality of measurement targets are often included in the analysis results, and as a result of maximizing the S/N ratio of the minimum peak, there is a case in which the S/N ratio of other peaks will be degraded. Therefore, the correction method for improving the S/N ratios of a plurality of peaks is preferable. In a case in which the S/N ratios of a plurality of peaks are improved using the correction method of (Method 1), since the absorption spectrum is different for each peak, a plurality of correction wavelengths is determined according to an extraction flow of the correction candidate wavelengths for each peak or each fixed zone. The detector output value fluctuation correction is executed before and after each peak or for each fixed zone using the plurality of correction wavelengths which are determined. Methods for using a plurality of peaks as targets are described in (Means 4) section in below.

(Method 2) In this method, in a case in which analysis is performed repeatedly under the same conditions, one wavelength of the correction wavelength at which reproducibility of the post-correction S/N ratio is most favorable from the correction candidate wavelengths, is selected, and the detector output value fluctuation correction process is executed.

After determining the correction target peak according to the correction target peak determination flow (F4b), the wavelength at which the reproducibility of the S/N ratio of the correction target peak is most favorable is selected from the extracted correction candidate wavelengths (F5c), and the detector output value fluctuation correction is executed based on the analysis flow (F6).

By performing the detector output value fluctuation correction at which the reproducibility of the S/N ratio of the minimum peak is most favorable using the detector output value fluctuation correction of this method, it becomes possible to perform qualitative and quantitative examination of the sample which includes a minute component with an emphasis on the reproducibility which is important when repeatedly measuring or the like.

(Method 3) Detector output value fluctuation correction method for selecting a plurality of correction wavelengths and executing the correction process with an emphasis on the reproducibility of the S/N ratio of the minimum peak is indicated.

Figure 4:
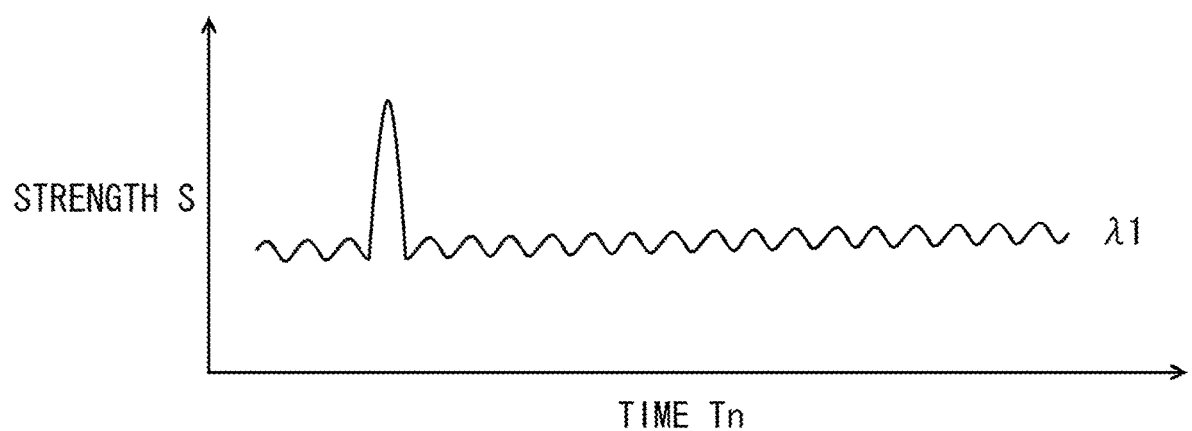
FIG. 4 is a detector output value display example (before correction) in the time Tn of the measurement wavelength $\lambda 1$.
Figure 5:
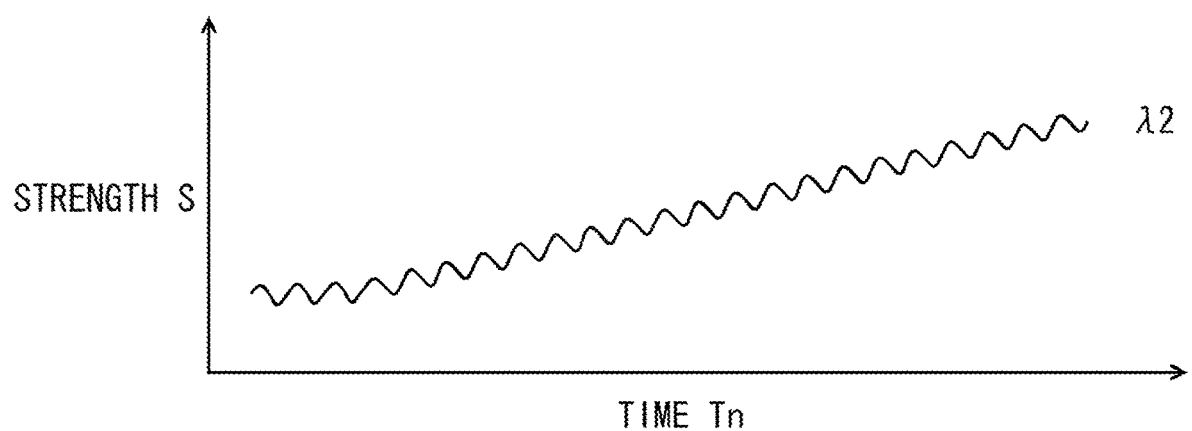
FIG. 5 is a detector output value display example (drifting present) in the time Tn of the correction candidate wavelength $\lambda 2$.
Figure 6:
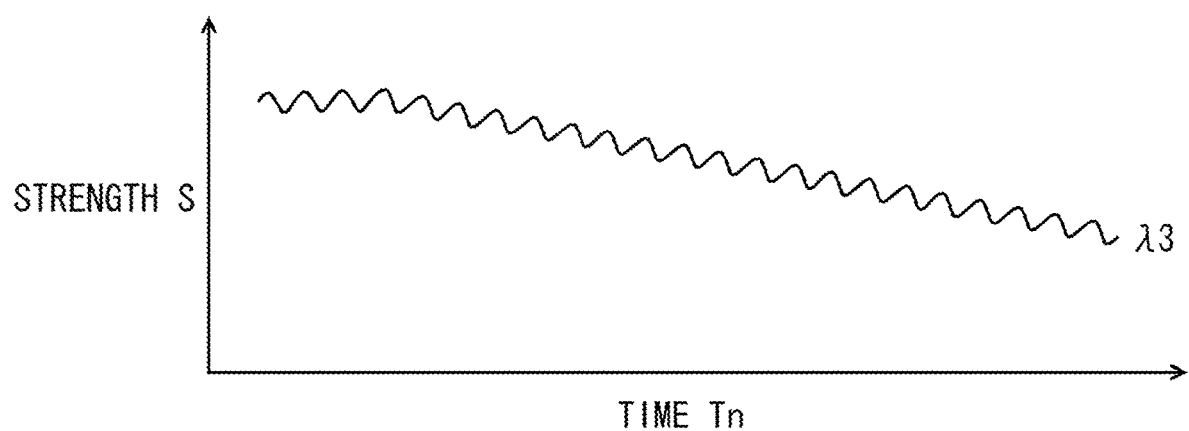
FIG. 6 is a detector output value display example (drifting present) in the time Tn of the correction candidate wavelength $\lambda 3$.
Figure 7:
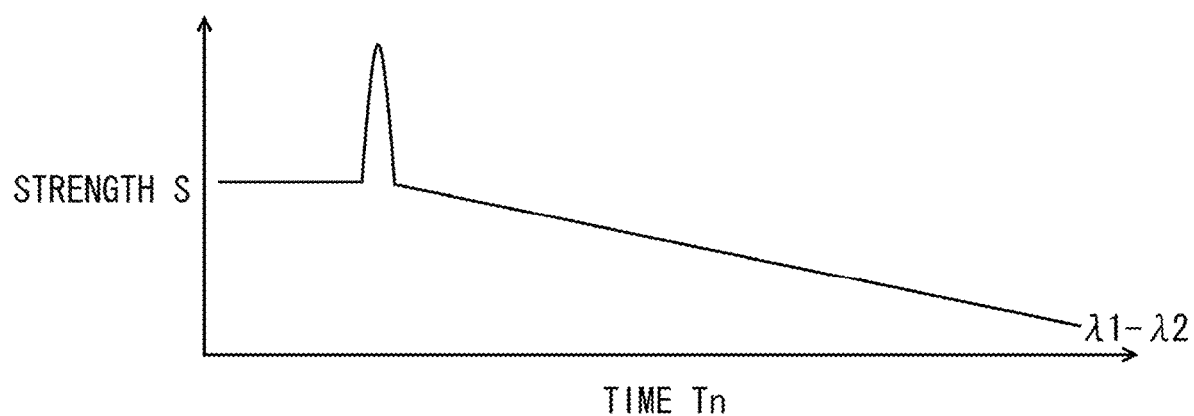
FIG. 7 is a detector output value display example (after correction using $\lambda 2$) in the time Tn of the measurement wavelength $\lambda 1$.
Figure 8:
FIG. 8 is a detector output value display example (after correction using an average value of $\lambda 2$ and $\lambda 3$) in the time Tn of the measurement wavelength $\lambda 1$.

For example, in a case in which the analysis results which are illustrated in FIGS. 4, 5, and 6 are obtained, when the signal of the wavelength λ2 of FIG. 5 is used for the detector output value fluctuation correction of the measurement wavelength λ1 of FIG. 4, according to the characteristics of drifting and the like of λ2, as illustrated in FIG. 7, the results are influenced by the characteristics of the correction wavelength which is used in the detector output value fluctuation correction. In order to avoid such unsuitable correction, it is possible to reduce the influence of drifting or the like which originates from an individual wavelength by using the average value of the signal strengths of the correction wavelengths λ2 and λ3 and obtain the suitable post detector output value fluctuation correction results which are illustrated in FIG. 8.

In this method, after determining the correction target peak according to the correction target peak determination flow (F4b), a correction wavelength in which there is not a plurality of peaks is selected (F5c) from the extracted correction wavelength candidates (F5b), and the detector output value fluctuation correction is performed using the average value of the selected plurality of correction wavelengths (F6).

It is also possible to perform the detector output value fluctuation correction using the average value of all wavelengths which have no peaks without selecting the correction wavelengths.

With this method, the detector output value fluctuation correction in which the reproducibility of the S/N ratio of the minimum peak is most favorable and in which the wavelength dependency is reduced is performed, and it is possible to perform qualitative and quantitative examination of the sample which includes minute components.

For the calculation of the average value, either a simple average or a weighted average is selected.

(Method 4) As the method for correcting detector output value fluctuation, a correction wavelength is selected for each detection peak which originates from the sample, and the detector output value fluctuation correction process in which the S/N ratio of each of the detection peaks which originate from the sample is greatest is performed.

After determining the correction target peak according to the correction target peak determination flow (F4b), the correction candidate wavelengths of each of the detection peaks which originate from the sample including the correction target peak are extracted (F5b), the correction wavelength at which the S/N ratio after the detector output value fluctuation correction process of each of the detection peaks which originate from the sample is greatest is selected (F5c), and the detector output value fluctuation correction is executed (F6).

In this method, since the minimum peak is recognized before the detector output value fluctuation correction, in the process of correcting the peaks which originate from other samples, it is possible to prevent the minimum peak from being buried in the correction process, and it is possible to perform the detector output value fluctuation correction on each of the detection peaks which originate from the sample which includes the minimum peak using the optimum correction wavelength, and to perform qualitative and quantitative examination of the sample which includes minute components.

(Method 5) In a case in which analysis is performed repeatedly under the same conditions, a correction wavelength at which the reproducibility of the S/N ratio after the correction in each of the detection peaks is most favorable is selected, and the detector output value fluctuation correction process is executed.

After determining the correction target peak according to the correction target peak determination flow (F4b), the correction wavelength at which the reproducibility of the S/N ratio of each of the correction target peaks which originate from the sample which includes the correction target peak is most favorable is selected (F5c), and the detector output value fluctuation correction is executed on each of the detection peaks (F6).

By using this method, it becomes possible to perform the detector output value fluctuation correction using the suitable correction wavelength for each of the detection peaks while emphasizing the reproducibility during repeated measurement. Since the minimum peak is recognized before the detector output value fluctuation correction, in the process of correcting the peaks which originate from other samples, it is possible to prevent the minimum peak from being buried in the correction process, and the detector output value fluctuation correction is performed on each of the detection peaks which originate from the sample which includes the minimum peak using the optimum correction wavelength, and so it is possible to perform qualitative and quantitative examination of the sample which includes minute components.

(Method 6) Since the wavelengths at which each of the absorption peaks appear are determined in the mobile phase (matter) which is used in the liquid chromatograph measurement, it is possible to create a database of peaks which originate from the mobile phase in each of the wavelengths. If the mobile phase which is used in the measurement is determined, it is possible to select the wavelength that can be used in the detector output value fluctuation correction from the database.

In the gradient elution method of the liquid chromatograph, two types of mobile phase are pumped while changing the flow rate ratio using a pump, and the absorbency or the like which is a physical property value of the mobile phase is influenced by mixing ripples caused by the gradient. Specifically, for example, in a case in which a mobile phase in which there is absorption in the measurement wavelength and a mobile phase in which there is not absorption in the measurement wavelength are used, a region in which there is absorption and a region in which there is not absorption are generated periodically due to the mixing state of the mobile phases, which becomes detector output value fluctuation.

Hereinafter, the detector output value fluctuation correction will be indicated with reference to the drawings.

Figure 9:
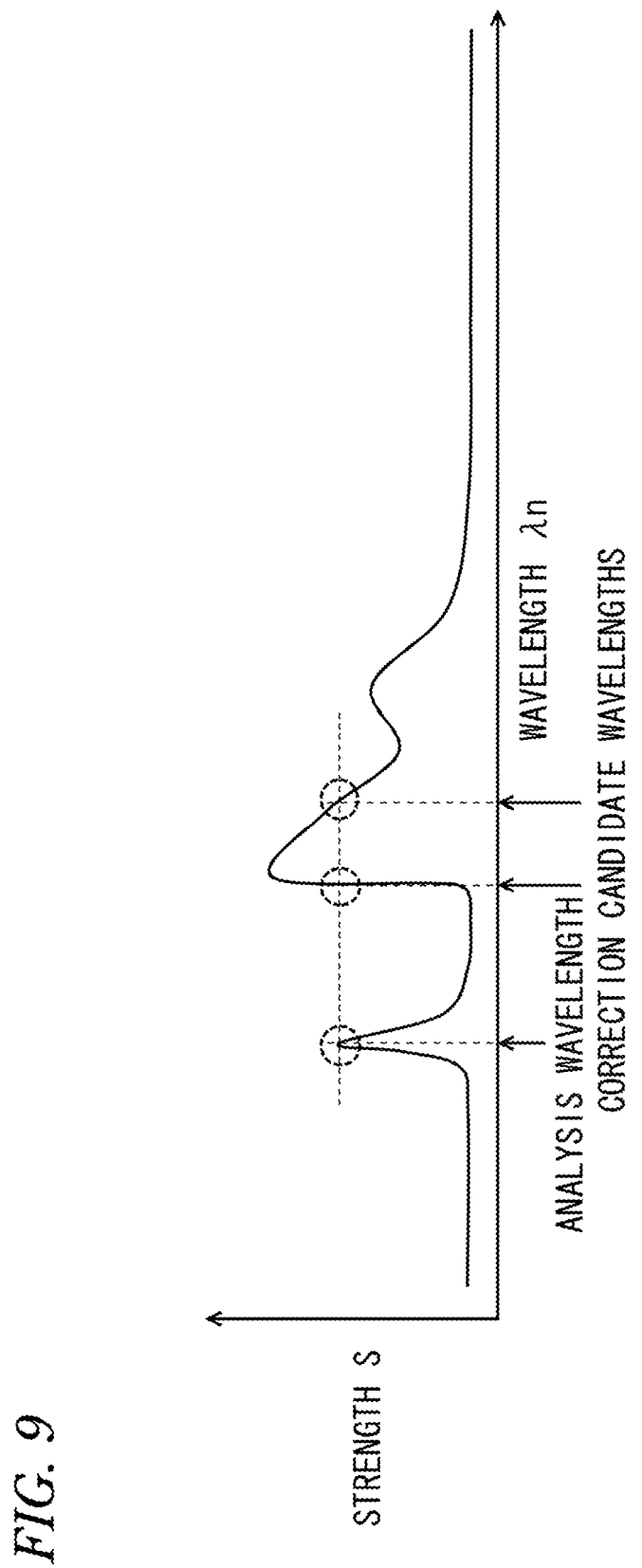
FIG. 9 is an absorption wavelength example and a correction wavelength selection example of mobile phases which are registered in a database.

FIG. 9 is an absorption spectrum of a mobile phase and is an example which is registered in the database. The magnitude of the periodic detector output value fluctuation which is caused by the mobile phase mixing is proportional to the signal strength of the absorption wavelength of the mobile phase which is illustrated in FIG. 9. For the correction wavelength which is used in the detector output value fluctuation correction, in a case in which there is no wavelength in which the signal strength of the absorption wavelength of the mobile phase is substantially equal to the signal strength of the measurement wavelength of the peak which originates from a sample or a wavelength in which the signal strength of the absorption wavelength of the mobile phase is substantially equal to the signal strength of the measurement wavelength of the peak which originates from the sample, the wavelength which is closer to the signal strength of the peak which originates from the sample is selected as the correction wavelength. Using the selected correction wavelength, the detector output value fluctuation correction of the peak which originates from the sample is performed including the correction target peak (F4b) which is determined according to the correction target peak determination flow. Since the correction wavelength is selected with respect to each of the peaks which originate from the sample, even if the peaks which originate from the sample are minute, the peaks are not buried by the detector output value fluctuation correction.

In this method, since the minimum peak is recognized before the detector output value fluctuation correction, in the process of correcting the peaks which originate from other samples, it is possible to prevent the minimum peak from being buried in the correction process, and since the detector output value fluctuation correction is performed by selecting the suitable correction wavelength which is based on the absorption spectrum of the mobile phase which is used for each of the measurement wavelengths of the peaks which originate from the sample, it is possible to perform qualitative and quantitative examination of the sample which includes minute components.

The detector output value fluctuation correction process of the present disclosure is not limited to the example, and may be performed by setting means 1 to an initial value (standard) and selecting one or a combination of multiple other means according to the object of the examination.

As described with reference to some examples in the above, by selecting and executing the registered measurement conditions and the method for correcting detector output value fluctuation according to the object of the analysis, it is possible to obtain qualitative and quantitative examination results with high sensitivity and good reproducibility with respect to a plurality or peaks or minute peaks which originate from minute components.

What is claimed is:

1. A method for correcting detector output value of a liquid chromatograph, the method comprising:

selecting an analysis condition for using a liquid chromatograph, the analysis condition being selected from preset recipes that are registered in advance according to an examination object, the analysis condition being a condition to be set with respect to devices included in the liquid chromatograph such as a pump, an auto sampler, a column oven, and a detector, starting analysis according to the analysis condition that is selected in the previous step, measuring a characteristic of a sample using the detector, the characteristic including at least one of an absorbency and a fluorescence amount, and storing and displaying a signal strength of the detector indicating the characteristic of the sample in relation to time as analysis results;

obtaining a chromatogram;

recognizing peaks included in the chromatogram;

determining a most minute peak of the signal strength of the analysis results in peaks which are recognized as a correction target peak;

determining correction candidate wavelengths with respect to the correction target peak;

performing a correction process on detector output value fluctuation based on correction method which is selected from among a plurality of preset correction methods; and outputting the analysis conditions, the correction condition, and corrected results of the characteristic of the sample.

2. The method of claim 1 further comprising:

selecting one wavelength of a correction wavelength at which an S/N ratio, which is a ratio between a detector output signal of the correction target peak and a detector output signal in the correction wavelength, is greatest and correcting the detector output signal of the correction target peak.

3. The method of claim 1 further comprising:
selecting one of a correction wavelength at which reproducibility of an S/N ratio is most favorable and correcting a detector output signal of the correction target peak.

4. The method of claim 1 further comprising:
selecting a plurality of correction wavelengths at which reproducibility of an S/N ratio is most favorable and correcting a detector output signal of the correction target peak using an average value of the detector output values in the plurality of selected wavelengths.

5. The method of claim 1 further comprising:
selecting each correction wavelength such that an S/N ratio of the correction target peak of each measurement target component is greatest and correcting a detector output signal of each of the correction target peaks.

6. The method of claim 1 further comprising:
selecting a plurality of correction wavelengths at which reproducibility of an S/N ratio of the correction target peak of each measurement target component is most favorable and correcting a detector output signal of the correction target peak using an average value of the detector output values in the plurality of selected wavelengths.

7. The method of claim 1 further comprising:
registering absorption wavelengths of a mobile phase which is used in liquid chromatography in advance as a database;
selecting correction wavelength from the database in accordance with the mobile phase being selected; and
correcting a detector output signal of the correction target peak using the selected correction wavelength.

* * * * *